(12) United States Patent
Gokaraju Ganga et al.

(10) Patent No.: US 8,541,381 B2
(45) Date of Patent: Sep. 24, 2013

(54) PROCESS FOR PRODUCING ENRICHED FRACTIONS CONTAINING UP TO 100% OF BACOPASAPONINS FROM THE PLANT MATERIALS OF BACOPA SPECIES

(75) Inventors: Raju Gokaraju Ganga, Andhra Pradesh (IN); Raju Gokaraju Rama, Andhra Pradesh (IN); Subbaraju Gottumukkala Venkata, Andhra Pradesh (IN); Trimurtulu Golakoti, Andhra Pradesh (IN); Sivaramakrishna Chillara, Andhra Pradesh (IN)

(73) Assignee: Laila Impex, Vijayawada, Andhra Pradesh (IN)

( * ) Notice: Subject to any disclaimer, the term of this patent is extended or adjusted under 35 U.S.C. 154(b) by 877 days.

(21) Appl. No.: 11/813,778

(22) PCT Filed: May 3, 2005

(86) PCT No.: PCT/IN2005/000138
§ 371 (c)(1),
(2), (4) Date: Jul. 12, 2007

(87) PCT Pub. No.: WO2006/117795
PCT Pub. Date: Nov. 9, 2006

(65) Prior Publication Data
US 2008/0132455 A1 Jun. 5, 2008

(51) Int. Cl.
*A61K 31/70* (2006.01)
*A61K 31/7028* (2006.01)
*C07H 17/00* (2006.01)

(52) U.S. Cl.
USPC .............. 514/25; 514/26; 536/18.5; 536/6

(58) Field of Classification Search
USPC .................. 514/25, 26; 536/18.5, 6
See application file for complete search history.

(56) References Cited

U.S. PATENT DOCUMENTS

| | | | |
|---|---|---|---|
| 6,361,804 B2 | 3/2002 | Singh-Verma | |
| 6,586,248 B2 | 7/2003 | Sangwan et al. | |
| 6,833,143 B1 | 12/2004 | Kahol et al. | |

FOREIGN PATENT DOCUMENTS

| | | | |
|---|---|---|---|
| WO | WO 2002/003803 A1 * | 1/2002 | |
| WO | 2004/054599 | 7/2004 | |
| WO | 2004/054599 A1 | 7/2004 | |
| WO | 2004/060267 A2 | 7/2004 | |
| WO | WO 2004/060267 A2 * | 7/2004 | |

OTHER PUBLICATIONS

Chatterjee, N., et al., Indian Journal of Chemistry, 1, 212-215, 1963.
Chatterjee, N., et al., Indian Journal of Chemistry, 3, 24-29, 1965.
Stough, C, et al., Psychopharmacology, 156, 481-484, 2001.
Abhang R., et al., Journal of Research in Ayurveda and Sidda, 14, 10-24, 1993.
Bacopa Monniera, Monograph, Alternative Medicine Review, 9, 79-85, 2000.
Singh, H.K., et al., Indian J Pharmacology, 29, S359-S365, 1997.
Chowdhuri, D.K., et al., Phytotherapy Research, 16, 639-645, 2002.
Bhattacharya SK, et al., Phytotherapy Research. 14, 174-179, 2000.
Enz, A., et al., Progress in Brain Research, 98, 431-438, 1993.
Singh, H.K., et al., Phytotherapy Research, 2, 70-75, 1988.
Deepak, M., et. al., Phytomedicine, 11, 264-268, 2004.
Ganzera, M., et al., Analytica Chimica Acta, 516, 149-154, 2004.
Deepak, M., et al., Phytochemical. Analysis, 16(1): 24-29, 2005.
D'Souza, P., et al., Phytotherapy Research, 16, 197-198, 2002.
Am. Chem. Soc. Symp. Series, 534, p. 114, 1992.
S.K. Bhattacharya et al., "Anxiolytic Activity of a Standardized Extract of *Bacopa monniera*: An Experimental Study." Phyomedicine, vol. 5, No. 2, 1998, pp. 77-82.
V. Elangovan et al., "In Vitro Studies on the Anticancer Activity of *Bacopa monnieri*." Fitoterapia, 1995, vol. 66, No. 3, pp. 211-215.
Jerry Loren McLaughlin et al., "'Bench-Top' Bioassays for the Discovery of Bioactive Natural Products: An Update." Studies in Natural Products Chemistry, vol. 9, 1991, pp. 383-385.
Jerry L. McLaughlin et al., "Simple Bench-Top Bioassays (Brine Shrimp and Potato Discs) for the Discovery of Plant Antitumor Compounds." American Chemical Society, Chapter 9, 1993, pp. 112-114.
Jerry L. McLaughlin et al., "The Use of Biological Assays to Evaluate Botanicals." Drug Information Journal, vol. 32, 1998, pp. 513-524.
G.D. Mukherjee et al., "Clinical Trial on BRAHMI-Part I." Journal of Experimental Medical Sciences, vol. 10, No. 1 and 2, Jun. and Sep. 1966, pp. 5-11.
R.H. Singh et al., "Studies on the Anti-Anxiety Effect of the Medhya Rasayana Drug, Brahmi (*Bacopa monniera* Wettst.)-Part I." Journal of Research in Ayurveda and Sidda, vol. 1, 1980, pp. 133-148.
R. Pal and J. P. S. Sarin, Quantitative Determination of Bacosides by UV-Spectrophotometry, Indian Journal of Pharmaceutical Sciences, 54 (1992) pp. 17-18.
Chillara Sivaramakrishna et al., "Triterpenoid glycosides from *Bacopa monnieri*," Phytochemistry, 66 (2005) 2719-2728.
Papolu Bhargava Sriramachandra Murthy et al., "Estimation of Twelve Bacopa Saponins in *Bacopa monnieri* Extracts and Formulations by High-Performance Liquid Chromatography," Chem. Pharm. Bull. 54(6) (2006) 907-911.
Ray Sahelian (editor), "Mind Boosters: A Guide to Natural Supplements That Enhance Your Mind, Memory, and Mood." St. Martin's Griffin, New York, 2000, pp. 167-167, 186-187 and 290-291.

* cited by examiner

*Primary Examiner* — Shaojia Anna Jiang
*Assistant Examiner* — Michael C Henry
(74) *Attorney, Agent, or Firm* — Fitch, Even, Tabin & Flannery, LLP

(57) ABSTRACT

This invention describes a process for producing a fraction enriched with jujubogenin and psudojujubogenin lycosides from *Bacopa* species, wherein the total *Bacopa* saponin concentration is up to 100% when estimated by HPLC method of analysis. The present invention also describes the processes for the enrichment of new compositions and individual saponin compounds from *Bacopa monnieri* to more than 95% purity. It further describes an analytical HPLC method for the estimation of total *Bacopa* saponin fraction and its use in therapeutic applications. This invention also includes two *Bacopa* saponin 3-O-[β-D-glucopyranosyl-(1→3)-β-D-glucopyranosyl] jujubogenin and 3-O-[β-D-glucopyranosyl-(1→3)-β-D-glucopyranosyl] pseudojujubogenin herein referred to as bacopaside N1 of general formula (1) and bacopaside N2 of general formula (2) respectively.

24 Claims, 1 Drawing Sheet

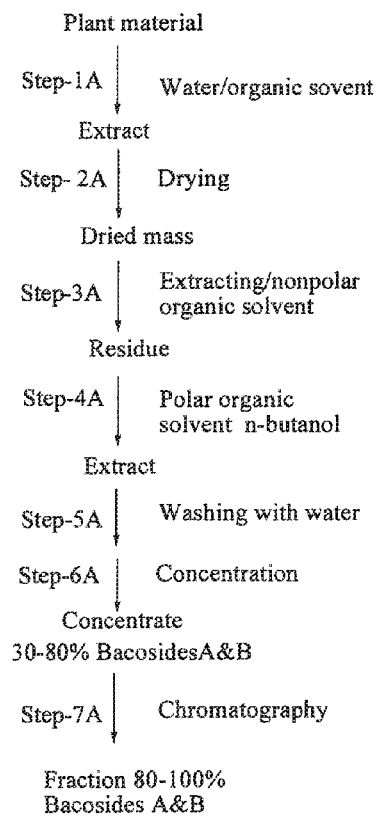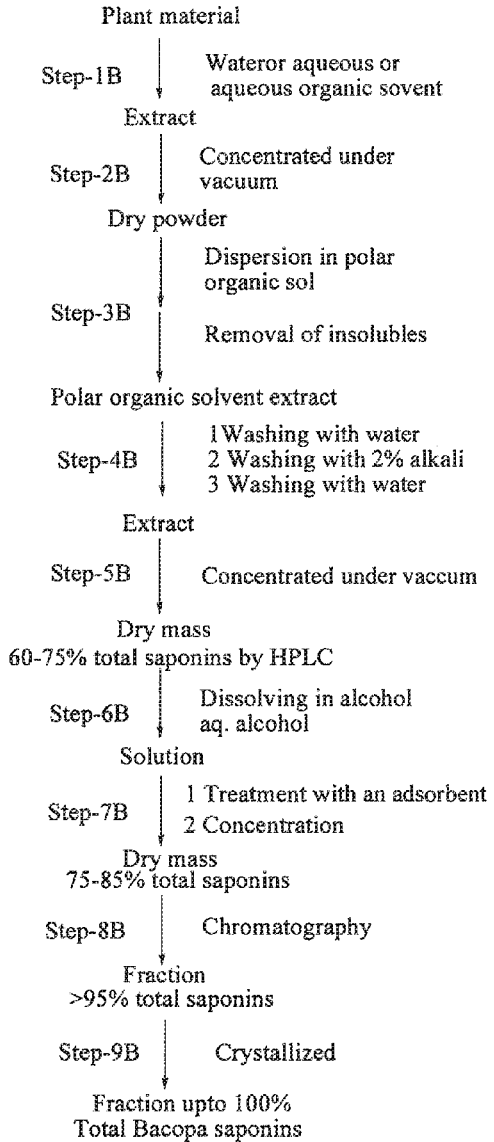

US 8,541,381 B2

PROCESS FOR PRODUCING ENRICHED FRACTIONS CONTAINING UP TO 100% OF BACOPASAPONINS FROM THE PLANT MATERIALS OF BACOPA SPECIES

TECHNICAL FIELD OF THE INVENTION

Memory has a direct bearing on one's mental capacity to think and reason. Losing control over the cognitive functions will adversely affect one's self-esteem, productivity and well-being. As people get older, many will experience considerable age related memory decline. This decline may range from simple benign forgetfulness to senile dementia. The search for an effective drug to improve and preserve memory is escalating. Pharmaceutical companies are investigating dozens of compounds to develop memory boosting "cognitive enhancers" that can prevent cognitive decline and preserve the ability to remember. There are a few herbal dietary supplements that contain various ingredients marketed for their ability to boost mental ability and enhance memory, the most notable of them are Gingko biloba, Nardostachys jatamansi, Acorus calamus, Centella asiatica and Bacopa monnieri.

Bacopa monnieri, widely known as "Brahmi" and water hyssop is a small, creeping herb with numerous branches, small oblong leaves, and light purple flowers. Brahmi grows naturally and very extensively in India in a wide range of altitudes. The Vedas, the ancient Indian science texts dated back to 5000 BC, have descriptions about Brahmi and it has been popularly known in the Ayurvedic system of medicine for centuries as an aid for enhancement of memory and mental agility (Mukheijee, G. D., et. al. *Journal of Experimental Medical Sciences*, 10, 5-11, 1966). It was used traditionally, as a brain tonic to enhance memory development, learning and concentration, and to provide relief to patients with anxiety or epileptic disorders. The plant has also been used in India and Pakistan as a cardiac tonic, digestive aid, and also to improve respiratory function in cases of bronchoconstriction.

BACKGROUND OF THE INVENTION

The double-blind and placebo-controlled clinical trials evaluated the acute and chronic effects of *Bacopa monnieri* on cognitive function in adults with respect to cognitive-enhancing effects, specifically memory, learning and concentration, and supported the traditional Ayurvedic claims attributed to it. The initial chemical investigations described the occurrence of two saponins, designated as bacosides A & B (Chatterjee, N., et al., Indian Journal of Chemistry, 1, 212-215, 1963, Chatteijee, N., et al., Indian Journal of Chemistry, 3, 24-29, 1965). A well designed 12 week study with 46 healthy human volunteers has shown that chronic administration of 300 mg of *Bacopa monnieri* extract standardized to 55% bacosides, is associated with cognitive-enhancing effects with a significant improvement in verbal learning, memory consolidation, and speed of early information processing in the treatment group compared to placebo (Stough, C., et. al., *Psychopharmacology*, 156, 481-484, 2001). The acute oral administrations of a single dose of 300 mg of *Bacopa monnieri* extract standardized to 55% bacosides, however showed no significant changes in cognitive function.

Bacopa's potential to modulate or enhance cognitive function has also been studied in children. A doudle blind placebo-controlled trial carried out on 110 school going children, in the age group of 10-13 using *Bacopa monnieri* has shown significant enhancement in memory (Abhang R., et. al. *Journal of Research in Ayurveda and Sidda*, 14, 10-24, 1993). A similar study with 36 children of attention deficit hyperactivity disorder (ADHD) conducted over a 16 week period with a treatment regime for 12 weeks with twice daily dose of 50 mg of *Bacopa* extract standardized to 20% bacosides showed significant improvements in sentence repetition, logical memory and paired associate learning tasks at 12 weeks and the effects maintained at 16 weeks (*Bacopa monniera*, monograph, *Alternative Medicine Review*, 9, 79-85, 2000).

Bacopa's potential as an anti-anxiety remedy has been supported by both animal and, clinical research. In an animal model, its anxiolytic activity was comparable to Lorazepam, a common benzodiazapene anxiolytic drug (Bhattacharya, S. K., et. al., *Phytomedicine*, 5, 77-82, 1998). A clinical trial of 35 patients with diagnosed anxiety neurosis demonstrated that administration of Brahmi syrup (equivalent to 12 g dry crude extract of *Bacopa*) resulted in a significant decrease in anxiety symptoms, level of anxiety, level of disability, and mental fatigue, and exhibited considerable increase in immediate memory span (Singh, R. H., et. al., *Journal of Research in Ayurveda and Sidda*, 1:133-148, 1980).

Other animal and human clinical studies support the beneficial actions of *Bacopa monnieri* on other indications as well, such as epilepsy, bronchitis, asthma, gastrointestinal disorders and hypothyroidism.

Mechanisms of action: A number of research studies have been initiated to study the mechanism behind Bacopa's therapeutic use for enhancement of cognitive function. The triterpenoid saponins and their bacosides were found to be responsible for Bacopa's ability to enhance nerve impulse transmission. The bacosides facilitate the repair of damaged neurons by enhancing kinase activity, neuronal synthesis, and restoration of synaptic activity, and ultimately nerve impulse transmission (Singh, H. K., et. al., *Indian J Pharmacology*, 29, S359-S365, 1997). *Bacopa* extracts modulate the expression of certain enzymes involved in the generation and scavenging of reactive oxygen species in the brain in experimental animals (Chowdhuri, D. K., et. al., *Phytotherapy Research*, 16, 639-645, 2002). These compounds facilitate the consolidation of the short-term memory and the effect persists even when the intermediate and long-term memories occur. Bacosides appear to have antioxidant activity in the hippocampus, frontal cortex, and striatum of the animals (Bhattacharya S K, et. al., *Phytotherapy Research.* 14, 174-179, 2000). As the loss of cholinergic neuronal activity in the hippocampus is the primary feature of Alzheimer's disease (Enz, A., et. al., *Progress in Brain Research*, 98, 431-438, 1993), bacosides may have a therapeutic effect in the treatment of Alzheimer's disease. The bacosides from *Boacopa mommieri* have the potential to exhibit antistress effects through modulating the activities of Hsp70, P450 and SOD, thereby possibly allowing the brain to be prepared to act under adverse conditions such as stress [Chowdhuri, D. K., et. al., *Phytotherapy Research.* 16, 639-645, 2002].

DISCLOSURE OF THE INVENTION

*Bacopa monnieri* has widely been used in herbal nutraceuticals for supporting brain and nerve function, enhancing memory, alertness and mental concentration [Ray Sahelian (editor), *Mind Boosters*, St. Martins Press, New York, 2000]. *Bacopa monnieri* extracts are also proven to be effective for the treatment of behavioural disorders, anxiety and conditions, where anxiety may play a role such as irritable bowel syndrome. The compounds responsible for the pharmacological effects of *Bacopa* include alkaloids, saponins and sterols. The cognitive enhancing benefits of *Bacopa monnieri* have been attributed to triterpenoid saponins, especially to the presence of two major dammarane saponins, namely, bacosides A and B (Singh, H. K., et. al, *Indian J Pharmacology*, 29, S359-S365, 1997 and Singh, H. K., et. al., *Phytotherapy Research*, 2, 70-75, 1988). The extracts standardized to bacosides were found to be safe in regulatory pharmacological and toxicological studies. No contraindications or cautions associated with *Bacopa* and bacosides have been reported. It was observed that the medicinal quality of the *Bacopa* preparations depends upon the presence and quality of these saponins.

The powder obtained on hydroalcohol extraction of *Bacopa monnieri* plant material contains over 10% saponin mixture of bacosides A and B. The chemical examination of *Bacopa monnieri* was first reported by Chatteiji, N., et. al. (*Indian J Chemistry*, 1, 212-215, 1963). Since then, a number of research articles have appeared describing the isolation and characterization of many saponin compounds (Deepak, M., et. al., *Phytomedicine*, 11, 264-268, 2004). Subsequently, further studies have established that bacosides A and B are in fact mixtures of di or triglycosides of jujubogenin or pseudo-jujubogenin, commonly known as dammarane type triterpenoid saponins (Deepak, M., et. al., *Phytochemical Analysis*, 16, 24-29, 2005).

There has been a great degree of confusion and many questions regarding the chemical identities of bacosides A and B, their quantitative estimation in the extracts and also optimum concentration of individual components in these mixtures for therapeutic efficacy (Deepak, M., et. al., *Phytomedicine*, 11, 264-268, 2004). Due to the apparent complexity in the molecular structure, a systematic isolation of the total spectrum of saponin compounds either from the *Bacopa* extracts or from bacosides A and B mixtures has been a difficult task. As the availability of pure authentic samples for individual *Bacopa* saponins is difficult, many *Bacopa* products available in the market with labeled claims on the content of bacosides A and B have been standardized by HPTLC and UV methods. These analytical methods, unfortunately, are rather vague and found to be highly prone to deviation from the absolute concentrations, as the standards themselves are mixtures. For example, a commercial sample of *B. monnieri* that was standardized to 50% bacosides A and B by UV method, in fact exhibited less than 20% of total *Bacopa* saponins, when estimated by HPLC against pure authentic samples (Ganzera, M., et. al., *Analytica Chimica Acta*, 516, 149-154, 2004).

The potential usefulness of *B. monnieri* in general and bacosides in particular has been a great incentive for further development of *Bacopa* saponins. An international patent application PCT WO 2004/054599 dated Jul. 1, 2004 filed by Gupta, M. M. et. al., describes a novel process for the preparation of bacosides enriched. in a non-hygroscopic form. Another PCT application (Gangaraju, G., et. al., PCT WO 2004/060267 dated Jul. 22, 2004), reported a process for producing up to 100% of bacosides A and B, wherein the mode of analysis was UV method. An efficient process for the industrial production of potential therapeutic composition of total *Bacopa* saponins, that possesses total absolute concentration up to 100% by HPLC method, is highly desirable and yet to be available in the literature.

As a part of the present investigation, we have accomplished the isolation of all twelve saponin components (chromatogram I), that are in recognizable quantities and include two previously unreported saponins, from the crude alcoholic extracts of *Bacopa monnieri* and rigorously established their chemical structures, using $^1$H NMR (Table 1), $^{13}$C NMR (Table 2) and mass spectral data. Having the authentic samples for the whole range of *Bacopa* saponins from *Bacopa monnieri* provided the first time opportunity to establish and standardize the total *Bacopa* saponin fraction standardized against pure authentic compounds especially by HPLC method.

The composition of bacoside A has been established very recently as a mixture of four triglycosidic saponins (Deepak, M., et. al., *Phytochemical. Analysis*, 16(1): 24-29, 2005) of general formula 5 to 8

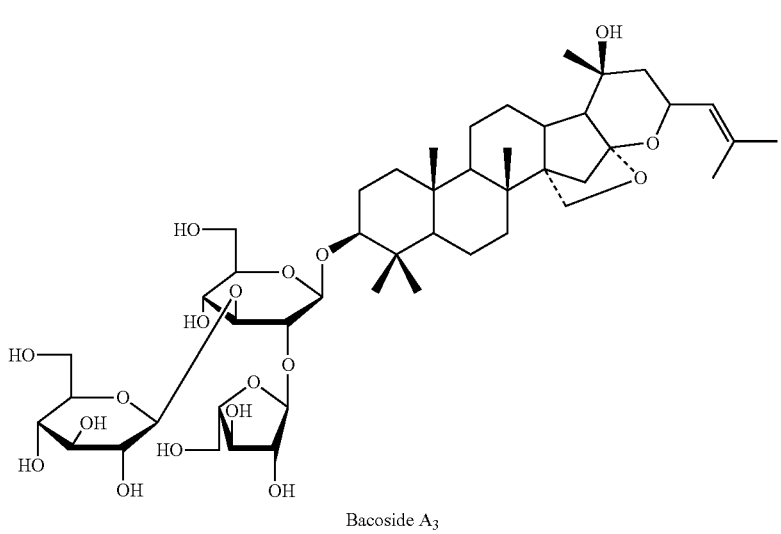

Bacoside A$_3$

-continued
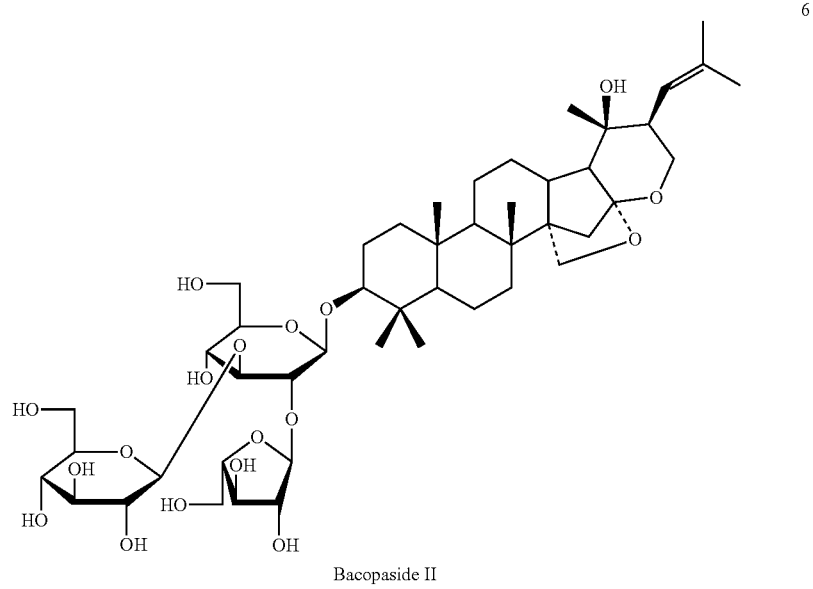
Bacopaside II
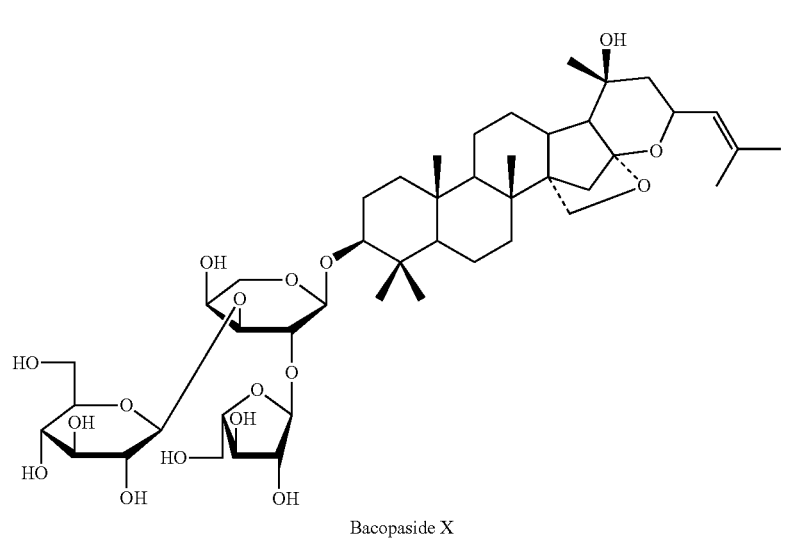
Bacopaside X

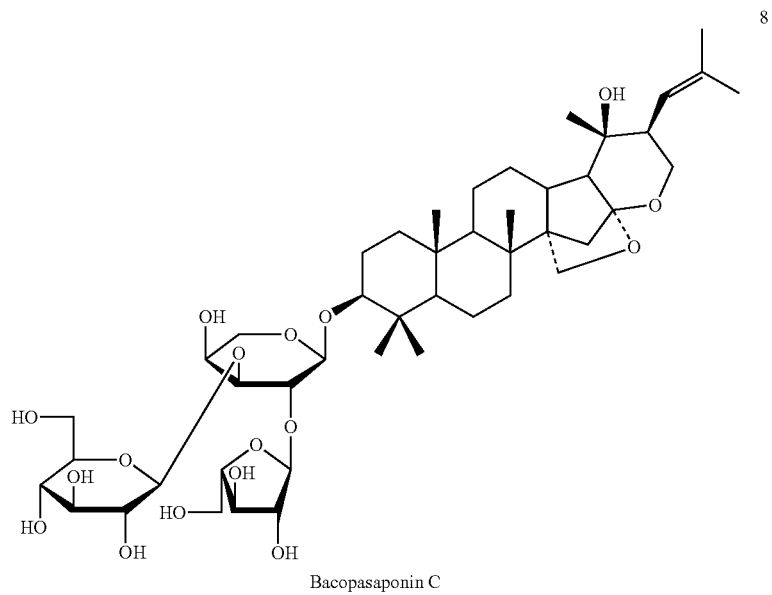
Bacopasaponin C
We have now confirmed by chemical analysis, this identity and established that bacoside B is composed of four diglycosidic saponins of general formula 1 to 4.
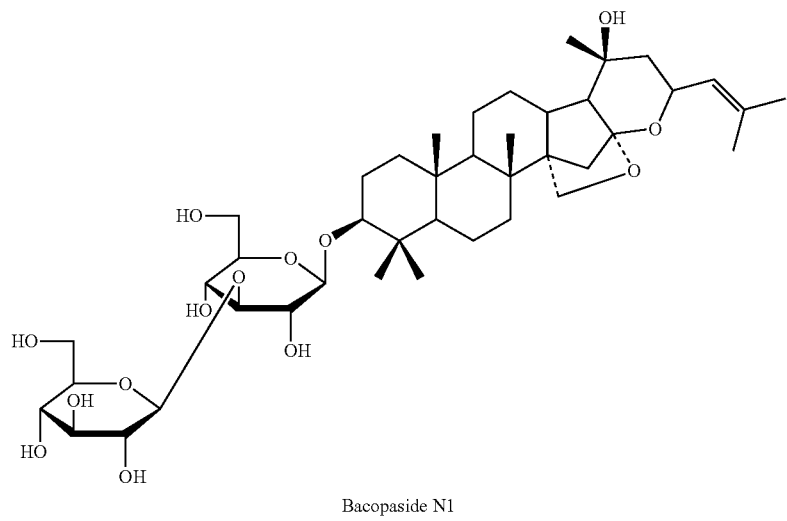
Bacopaside N1

-continued
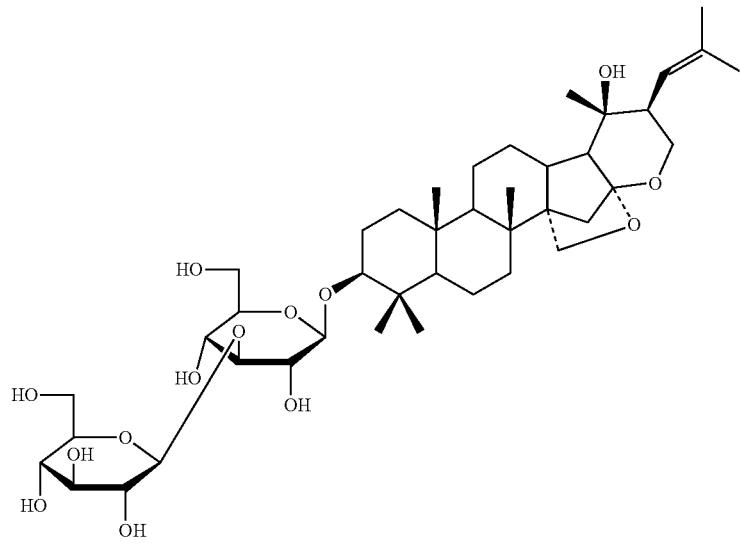
Bacopaside N2
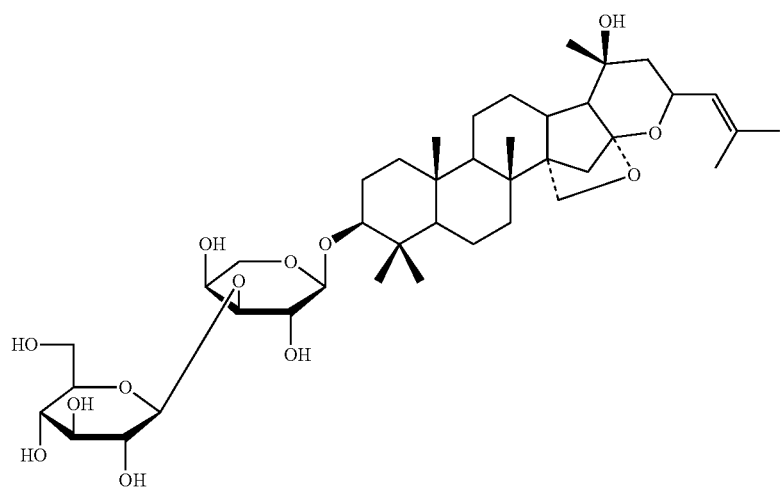
Bacopaside IV
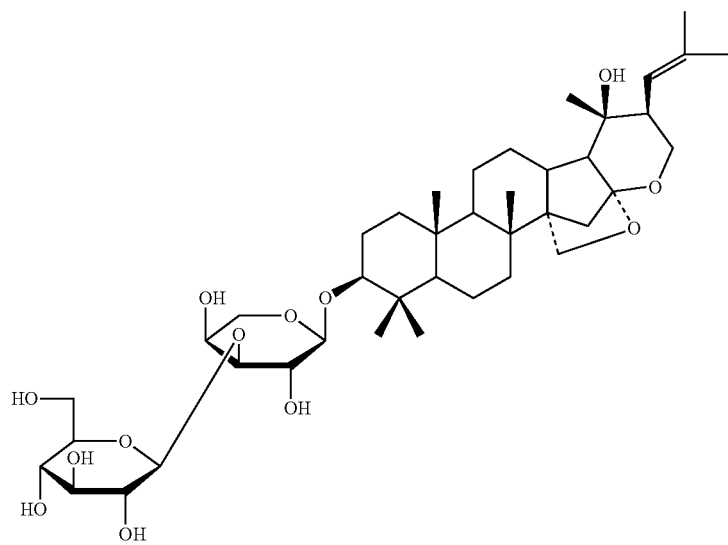
Bacopaside V Interestingly, two of these metabolites 1 and 2 are new compounds and they are reported for the first time as part of this invention. Other compounds of *Bacopa* saponin fraction include two sulfur compounds bacopaside I of general formula (9)

and bacopaside III of general formula (10)

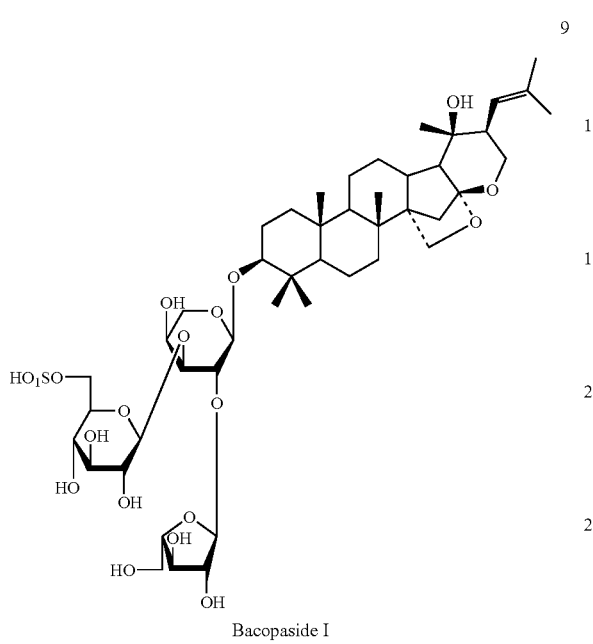

Bacopaside I

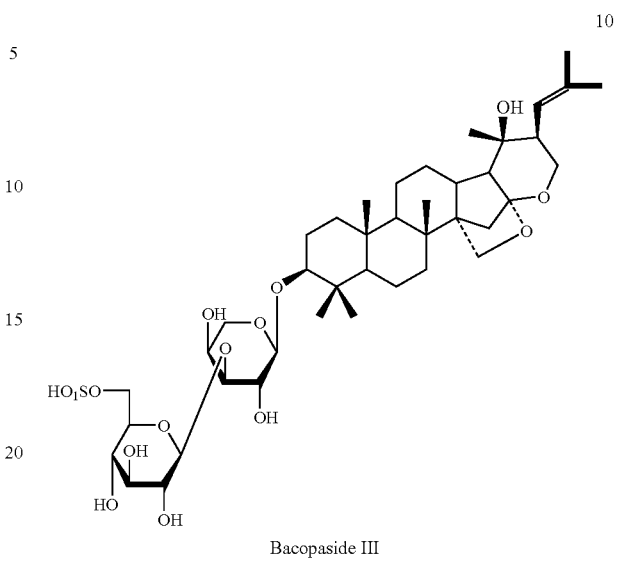

Bacopaside III that are sulfated compounds of bacopasaponin C and bacopaside IV respectively, and two tetraglycosidic saponins, bacopasaponin E of general formula

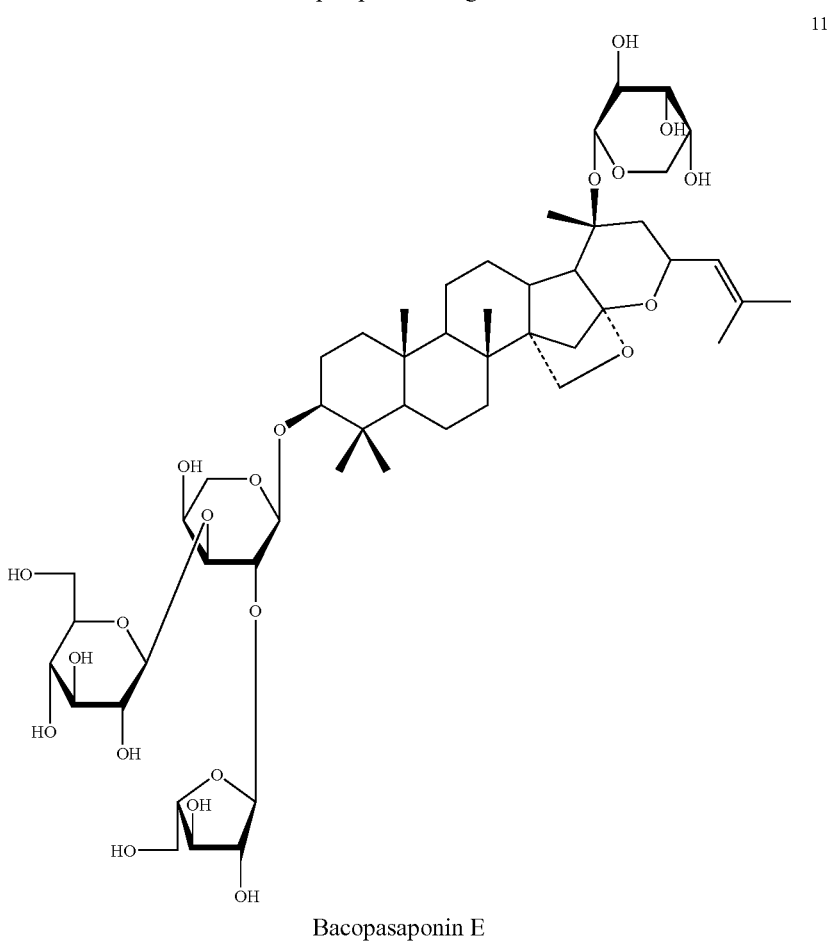

Bacopasaponin E and bacopasaponin F of general formula

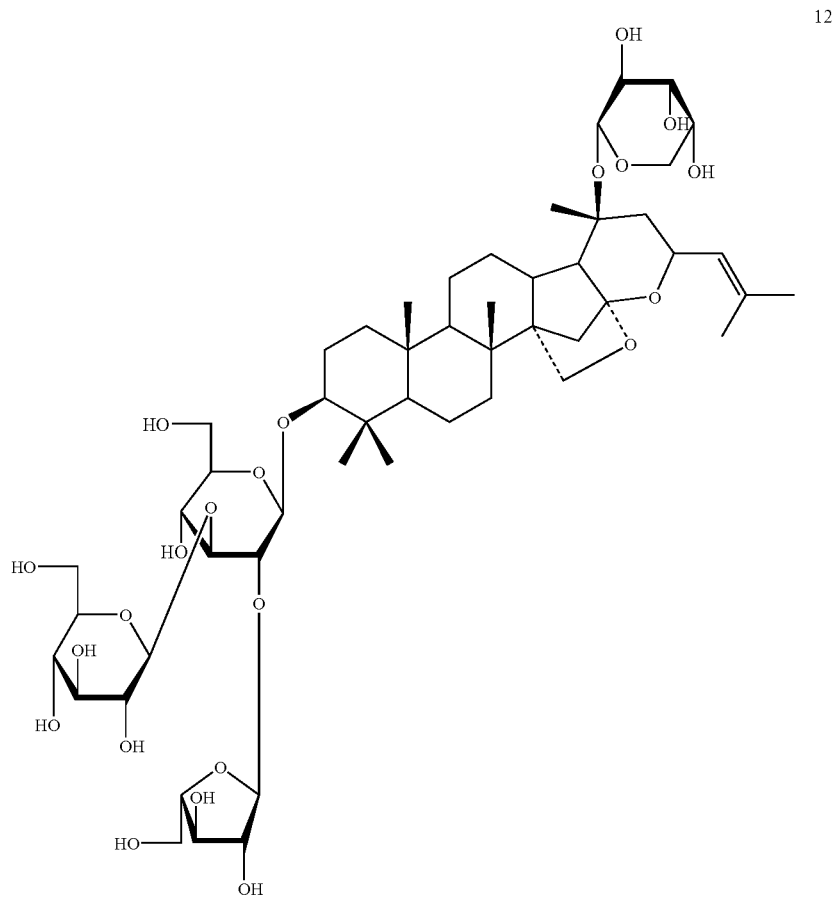

Bacopasaponin F

The present invention has been aimed at selective enrichment of total *Bacopa* saponins, the bioactive metabolites of *Bacopa monnieri*. The primary aspect of this invention is a process for an improved fraction that show by an HPLC method of analysis, up to 100% total absolute concentration of jujubogenin and pseudojujubogenin glycosides and include two previously unknown saponins.

This commercially feasible process has been possible due to the introduction of two simple but crucial non-obvious steps newly adapted for the phytochemical study of *Bacopa*. A significant improvement in total *Bacopa* saponin concentration (25-35% to 60-75%) has been accomplished by giving an aqueous alkali wash to the polar organic solvent extractives of *Bacopa* crude extract. A further significant enrichment of total *Bacopa* saponins (60-75% to 80-85%) was the result of a charcoal treatment to the said alkali washed bacopa saponin fraction. A fraction enriched up to 100% of total *Bacopa* saponins has been achieved by subjecting the charcoal treated *Bacopa* saponin fraction to flash chromatography on normal silica gel or reversed phase gel followed by crystallization of *Bacopa* saponin fractions.

The present invention also describes the isolation and characterization of two new saponins, 3-O-[β-D-glucopyranosyl-(1→3)-β-D-glucopyranosyl] jujubogenin of general formula (1)

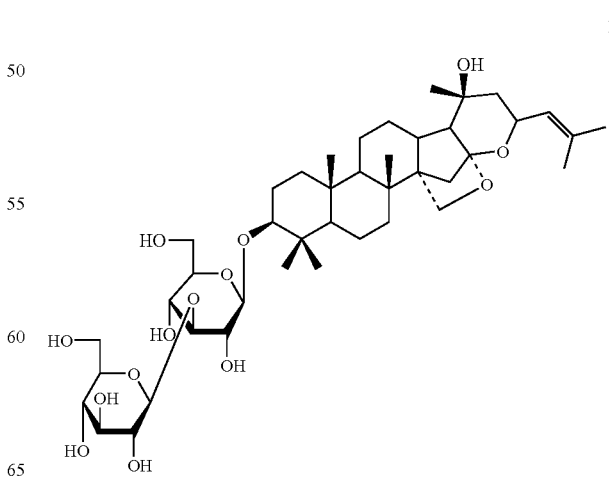

Bacopaside N1 and 3-O-[β-D-glucopyranosyl-(1→3)-β-D-glucopyranosyl] pseudojujubogenin of general of general formula (2)

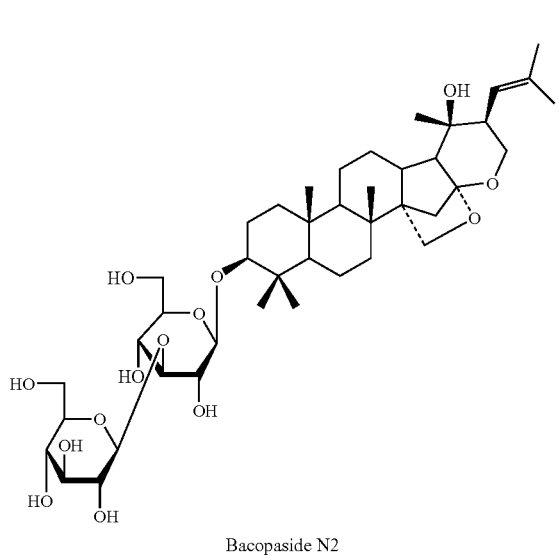

Bacopaside N2 labeled as bacopaside N1 and bacopaside N2 respectively, along with 10 known *Bacopa* saponins of general formulae 3 to 12.

In the other aspect, this invention presents the potential usefulness of enriched compositions in therapeutic applications. Many beneficial actions of *Bacopa munnieri* have been presumed to be due to the presence of saponin compounds in extracts. *Bacopa* extracts and fractions were found to inhibit Brine shrimp, Artemia salina (DSouza, P., et. al., *Phytotherapy Research*, 16, 197-198, 2002). The Brine shrimp lethality is generally considered as an indication for cytotoxicity (McLaughlin, J. L., et. al., *Drug Information Journal*, 32, 513-524, 1998). *Bacopa* saponin fractions have infact demonstrated cytotoxic activity against sarcoma-180 cancer cells (Elangovan, V., et. al., *Fitoterapia* 1995; 66, 211-215, 1995). To investigate the potential effect of enrichment on therapeutic efficasy, we have evaluated the Brine shrimp lethality of *Bacopa* extracts and enriched fractions. The data (Table 3) indicate that the magnitude of inhibition was found to depend on total *Bacopa* saponin concentration. For example a sample enriched to 97% *Bacopa* saponins is more potent than a sample enriched to 80% saponins, which in turn is more potent than a commercial sample of *Bacopa* standardized to 50% bacosides A and B, and also crude extract with 14.8% of total *Bacopa* saponins.

The present invention further describes an analytical HPLC method for the quantitative estimation of total *Bacopa* saponin concentration. The total saponin content in the enriched fractions is considerably higher than that of the commercial samples of *Bacopa* and comprised of novel glycosides, previously unreported. The typical HPLC chromatogram for an enriched fraction containing the saponins of general formula 1 to 12 is given in chromatogram (FIG. 1)

EXAMPLE 1

Purification of individual compounds: The air-dried and powder plant material (350 g) was extracted with 70% methanol under reflux for 4 h. The plant material was removed by filtration and the extract was concentrated under vacuum. The dark colored residue (200 g) was dissolved in 1 L of n-butanol and washed with water. The n-butanol layer was evaporated and dried under vacuum to obtain a thick paste (82 g). The ethyl acetate extractives were removed from the thick paste under reflux and the residue (120 g) subjected to column chromatography over silica gel using eluants of increasing polarity starting from chloroform to methanol. The fractions that were eluted with chloroform/methanol 8.5:1.5 yielded a mixture of four diglycosidic saponins (9.5 g), the fraction eluted with chloroform/methanol 8:2 yielded a mixture of four triglycosidic saponins (29.0 g), the fractions eluted with chloroform/methanol/water 8:2:0.03 yielded a mixture of two sulfated saponins (5.0 g) and finally the fraction eluted with chloroform/methanol/water 8:2:0.5 yielded a mixture of two tetraglycosidic saponins (1.5 g). The diglycosidic saponins mixture (3.0 g) was found to be a mixture of four components by HPLC analysis. It was subjected to rechromatography over reversed phase polymer resin (MCI GEL® CHP20P, 75-150μ, Mitsubishi Chemical Corporation, Tokyo, Japan) using 7:3 methanol/water mixture to yield two new compounds, 3-O-[O-D-glucopyranosyl-(1→3)-β-D -glucopyranosyl] jujubogenin (bacopaside N1, of general formula 1) and 3-O-[β-D-glucopyranosyl-(1→3)-β-D -glucopyranosyl] pseudojujubogenin (bacopaside N2, of general formula 2) along with two known saponins 3-O-[β-D-glucopyranosyl-(1→3)-α-L-arabinopyranosyl] jujubogenin (bacopaside IV, of general formula 3) and 3-O-[β-D-glucopyranosyl-(1→3)-α-L-arabinopyranosyl] pseudojujubogenin (bacopaside V, of general formula 4) in partially pure form. These partially pure compounds were further subjected to rechromatography on reversed phase resin column under similar conditions to obtain the compound of general formula 1 (200 mg), the compound of general formula 2 (250 mg), the compound of general formula 3 (120 mg) and the compound of general formula 4 (140 mg). The triglycosidic saponins mixture (7 g) was subjected to flash chromatography over reversed phase polymer resin (MCI GEL® CHP20P, 75-150μ, Mitsubishi Chemical Corporation, Tokyo, Japan) using solvents of decreasing polarity from 1:1 methanol/water mixture to 7:3 methanol/water mixture to afford four known saponins, 3-O-[β-D-glucopyranosyl-(1→3)-O-{α-L-arabinofuranosyl-(1→2)}-O-(β-D-glucopyranosyl)] jujubogenin (bacoside $A_3$, of general formula 5, 90 mg), 3-O-[α-L-arabinofuranosyl-(1→2)-{β-D-glucopyranosyl-(1→3)}-β-D-glucopyranosyl] pseudojujubogenin (bacopaside II, of general formula 6, 400 mg), 3-O-[α-L-arabinofuranosyl-(1→2)-{β-D-glucopyranosyl-(1→3)-}-α-L-arabinopyranosyl] jujubogenin (of general formula 7, 100 mg), 3-O-[β-D-glucopyranosyl-(1→3)-{α-L-arabinofuranosyl-(1→2)}-α-L-arabinopyranosyl] pseudojujubogenin (bacopasaponin C, of general formula 8, 240 mg) as pure compounds and further quantities of these materials as mixtures. The sulfated *Bacopa* saponin fraction (1.4 g) was subjected to rechromatography over silica gel using chloroform/methanol/water (8.2:1.8:0.02) to yield two pure saponins, 3-O-[α-L-arabinofuranosyl-(1→2)-{6-O-sulphonyl-β-D-glucopyranosyl-(1→3)}-α-L-arabinopyranosyl] pseudojujubogenin (bacopaside I, of general formula 9, 80 mg) and 3-O-[{6-O-sulfonyl-β-D-glucopyranosyl-(1→3)}-α-L-arabinopyranosyl] pseudojujubogenin (bacopaside III, of general formula 10, 80 mg). The tetraglycosodic fraction was subjected to normal phase silica chromatography followed by further purification on reversed phase polymer resin (MCI GEL® CHP20P, 75-150μ, Mitsubishi Chemical Corporation, Tokyo, Japan) using solvents of decreasing polarity from 1:1 methanol/water mixture to 8:2 methanol/water to afford two known dammarane type jujubogenin bisdesmosides, 3-O-[β-

D-glucopyranosyl-(1→3)-{-α-L-arabinofuranosyl-(1→2)}-α-L-arabinopyranosyl]-20-O-(α-L-arabinopyranosyl) jujubogenin (bacopasaponin E, of general formula 11, 320 mg) and 3-O-[β-D-glucopyranosyl-(1→3)-{α-L-arabinofuranosyl-(1→2)}-β-D-glucopyranosyl]-20-O-(α-L-arabinopyranosyl)] jujubogenin (bacopasaponin F, of general formula 12, 380 mg).

3-O-[β-D-glucopyranosyl-(1→3)-(3-D-glucopyranosyl] jujuboyenin (bacopaside N1, of general formula 1) . Melting point: 256-260° C.; IR (KBr): 3430, 2925, 2855, 1633, 1451, 1380, 1290, 1250, 1078, 1035 cm⁻¹; LC-MS (negative) m/z 795 (M-H)⁻; LC-MS (positive) m/z 819 (M+Na)⁺; $^1$H NMR data is given in table 1 and $^{13}$C NMR is given in table 2.

3-O-[β-D-glucopyranosyl-(1→3)-β-D-glucopyranosyl] pseudojujubogenin (bacopaside N2 of general formula 2): Melting point: 278-282° C.; IR (KBr): 3435, 2928, 2860, 1639, 1453, 1378, 1288, 1213, 1078, 1035 cm⁻¹; LC-MS (positive) m/z 819 (M+Na)⁺; $^1$H NMR data is given in table 1 and $^{13}$C NMR is given in table 2.

3-O-[β-D-glucopyranosyl-(1→3)-α-L-arabinopyranosyl] jujubogenin (bacopaside IV, of general formula 3): Melting point: 266-270° C.; LC-MS (negative) m/z 765 (M-H)³¹ ; $^1$H NMR data is given in table 1 and $^{13}$C NMR is given in table 2.

3-O-[β-D-glucopyranosyl-(1→3)-α-L-arabinopyranosyl] pseudojujubogenin (bacopaside V, of general formula 4): Melting point: 274-278° C.; IR (CHCl₃): 3432, 2941, 1625, 1444, 1380, 1287, 1213, 1075, 1030 cm⁻; LC-MS (positive) m/z 765 (M-H)³¹; $^1$H NMR data is given in table 1 and $^{13}$C NMR is given in table 2.

3-O-[β-D-glucopyranosyl-(1 3)-O-{α-L-arabinofuranosyl-(1→2)}-O-(β-D-glucopyranosyl)] jujubogenin (bacoside A₃,of general formula 5): LC-MS (negative) m/z 927 (M-H)⁻; $^1$H NMR data is given in table 1 and $^{13}$C NMR is given in table 2.

3-O-[α-L-arabinofuranosyl-(1→2)-{β-D-glucopyranosyl-(1→3)}-β-D-glucopyranosyl] pseudojujubogenin (bacopaside II, of general formula 6): Melting point: 256-262° C.; IR (KBr): 3431, 2940, 1638, 1453, 1374, 1287, 1214, 1078, 1034 cm⁻¹; LC-MS (negative) m/z 927 (M-H)⁻; $^1$H NMR data is given table 1 and $^{13}$C NMR is given in table 2.

3-O-[α-L-arabinofuranosyl-(1→2)-{β-D-glucopyranosyl-(1→3)-}-α-L-arabinopyranosyl] jujubogenin (bacopaside X, of general formula 7): Melting point: 228-233° C.; LC-MS (negative) m/z 897 (M-H)⁻; $^1$H NMR data is given in table 1 and $^{13}$C NMR is given in table 2.

3-O-[β-D-glucopyranosyl-(1→3)-{α-L-arabinofuranosyl-(1→2)}-α-L-arabinopyranosyl] pseudojujubogenin (bacopasaponin C, of general formula 8): Melting point: 320-322° C.; IR (KBr): 3410, 2942, 1596, 1451, 1385, 1287, 1214, 1075, 1028 cm⁻¹; LC-MS (negative) m/z 897 (M-H)⁻; $^1$H NMR data is given in table 1 and $^{13}$C NMR is given in table 2.

3-O-[α-L-arabinofuranosyl-(1→2)-{6-O-sulphonyl-β-D-glucopyranosyl-(1→3)}-α-L-arabinopyranosyl] pseudojujubogenin (bacopaside I, of general formula 9): Melting point: 262-261° C.; LC-MS (negative) m/z 977 (M-H)⁻; $^1$H NMR data is given table 1 and $^{13}$C NMR is given in table 2.

3-O-[{6-O-sulfonyl-β-D-glucopyranosyl-(1 3)-α-L-arabinopyranosyl] pseudojujubogenin (bacopaside III, of general formula 10): LC-MS (negative) m/z 845 (M-H)⁻; $^1$H NMR data is given table 1 and $^{13}$C NMR is given in table 2.

3-O-[β-D-glucopyranosyl-(1→3)-{α-L-arabinofuranosyl-(1→2)}-α-L-arabinopyranosyl]-20-O-(α-L-arabinopyranosyl) jujubogenin (bacopasaponin E, of general formula 11): Melting point: 248-256° C.; IR (KBr): 3408, 2941, 2872, 1640, 1452, 1374, 1291, 1262, 1214, 1079, 1028 cm⁻¹; LC-MS (positive) m/z 1053 (M+Na)⁺; $^1$H NMR data is given in table 1 and $^{13}$C NMR is given in table 2.

3-O-[β-D-glucopyranosyl-(1→3)-{α-L-arabinofuranosyl-(1→2)}-β-D-glucopyranosyl]-20-O-(α-L-arabinopyranosyl)] jujubogenin (bacopasaponin F, of general formula 12): Melting point: 246-258° C.; IR (KBr): 3410, 2941, 2874, 1651, 1453, 1374, 1290, 1254, 1243, 1080, 1004 cm⁻¹; LC-MS (positive) m/z 1083 (M+Na)⁺; $^1$H NMR data is given in table 1 and $^{13}$C NMR is given in table 2.

TABLE 1

$^1$H NMR data of *Bacopa* Saponins

| S. No. | Proton | 1 | 2 | 3 | 4 | 5 | 6 | 7 | 8 | 9 | 10 | 11 | 12 |
|---|---|---|---|---|---|---|---|---|---|---|---|---|---|
| 1 | H₃-18 | 1.05 | 1.06 | 1.07 | 1.08 | 1.08 | 1.04 | 1.06 | 1.05 | 1.04 | 1.07 | 1.037 | 1.03 |
| 2 | H₃-19 | 0.69 | 0.69 | 0.74 | 0.75 | 0.67 | 0.67 | 0.78 | 0.69 | 0.68 | 0.74 | 0.64 | 0.62 |
| 3 | H₃-21 | 1.37 | 1.37 | 1.38 | 1.39 | 1.39 | 1.38 | 1.38 | 1.38 | 1.37 | 1.36 | 1.40 | 1.41 |
| 4 | H₃-26 | 1.67 | 1.67 | 1.69 | 1.69 | 1.69 | 1.61 | 1.67 | 1.64 | 1.67 | 1.68 | 1.67 | 1.67 |
| 5 | H₃-27 | 1.65 | 1.65 | 1.67 | 1.62 | 1.66 | 1.61 | 1.69 | 1.58 | 1.59 | 1.61 | 1.80 | 1.80 |
| 6 | H₃-28 | 1.27 | 1.27 | 1.30 | 1.30 | 1.29 | 1.29 | 1.28 | 1.21 | 1.24 | 1.27 | 1.25 | 1.25 |
| 7 | H₃-29 | 0.97 | 0.97 | 0.98 | 0.98 | 1.05 | 1.10 | 1.07 | 1.0 | 1.03 | 0.95 | 0.95 | 0.94 |
| 8 | H₃-30 | 4.20 | 4.21 | 4.21 | 4.22 | 4.21 | 4.12 | 4.3 | 4.21 | 4.18 | 4.19 | 4.21 | 4.22 |
| 9 | H₃-23 | 5.20 | 3.87 | 5.20 | 3.89 | 5.20 | 3.87 | 5.22 | 3.79 | 3.85 | 3.87 | 5.34 | 5.33 |
| 10 | H-3 | 3.33 | 3.32 | 3.33 | 3.23 | 3.27 | 3.27 | 3.25 | 3.06 | 3.24 | 3.33 | 3.22 | 3.23 |
| 11 | H-13 | 2.81 | 2.82 | 2.82 | 2.86 | 2.83 | 2.84 | 2.84 | 3.25 | 2.84 | 2.86 | 5.48 | 5.48 |
| 12 | H-24 | 5.50 | 5.83 | 5.82 | 5.85 | 5.83 | 5.83 | 5.54 | 5.84 | 5.89 | 5.84 | 4.74 | 4.77 |
| 13 | H-1' | 4.51 | 4.53 | 4.76 | 4.77 | 4.29 | 4.83 | 4.8 | 4.72 | 4.88 | 4.77 | 4.84 | 4.53 |
| 14 | H-2' | 4.05 | 4.03 | 4.61 | 4.62 | 4.03 | 4.04 | 4.52 | 4.30 | 4.53 | 4.54 | 4.50 | 4.12 |
| 15 | H-3' | 4.07 | 4.19 | 4.24 | 4.25 | 4.14 | 4.14 | 4.23 | 4.21 | 4.21 | 4.24 | 4.23 | 4.05 |
| 16 | H-4' | 4.20 | 4.52 | 4.45 | 4.45 | 3.93 | 3.93 | 4.51 | 4.49 | 4.59 | 4.54 | 4.51 | 4.16 |
| 17 | H-5' | 3.93 | 3.93 | 3.75 | 3.75 | 3.88 | 3.82 | 4.21 | 4.23 | 3.73 | 3.77 | 4.41 | 4.57 |
| 18 | H-1" | 5.29 | 5.29 | 5.42 | 5.41 | 6.30 | 6.30 | 6.12 | 6.13 | 6.09 | 5.16 | 5.13 | 5.19 |
| 19 | H-2" | 4.05 | 4.05 | 4.05 | 4.05 | 5.07 | 5.08 | 5.05 | 4.95 | 4.91 | 3.86 | 3.94 | 3.97 |
| 20 | H-3" | 4.28 | 4.23 | 4.24 | 4.25 | 4.85 | 4.84 | 4.91 | 4.78 | 4.87 | 4.11 | 3.73 | 3.72 |
| 21 | H-4" | 4.05 | 4.03 | 4.25 | 4.01 | 4.75 | 4.74 | 4.82 | 4.72 | 4.73 | 4.11 | 4.10 | 4.07 |
| 22 | H-5" | 4.28 | 4.28 | 4.40 | 4.57 | 4.21 | 4.17 | 4.33 | 4.24 | 4.24 |  | 4.04 | 3.95 |
| 23 | H-1''' | 4.51 | 4.52 |  |  | 5.35 | 5.18 | 5.16 | 5.07 | 4.91 |  | 6.08 | 6.17 |
| 24 | H-2''' |  |  |  |  | 4.00 | 3.98 | 3.97 | 3.89 | 3.78 |  | 5.01 | 5.02 |
| 25 | H-3''' |  |  |  |  | 4.14 | 4.16 | 4.23 | 4.19 | 4.14 |  | 4.88 | 4.82 |
| 26 | H-4''' |  |  |  |  | 4.03 | 4.06 | 4.19 | 3.98 | 4.18 |  | 4.21 | 4.18 |

TABLE 1-continued

¹H NMR data of *Bacopa* Saponins

| S. No. | Proton | 1 | 2 | 3 | 4 | 5 | 6 | 7 | 8 | 9 | 10 | 11 | 12 |
|---|---|---|---|---|---|---|---|---|---|---|---|---|---|
| 27 | H-5''' | | | | | 3.88 | 3.86 | 3.97 | 3.87 | 4.01 | | 4.32 | 4.27 |
| 28 | H-1'''' | | | | | | | | | | | 4.74 | 4.82 |

TABLE 2

¹³C NMR data of *Bacopa* Saponins

| C | 1 | 2 | 3 | 4 | 5 | 6 | 7 | 8 | 9 | 10 | 11 | 12 |
|---|---|---|---|---|---|---|---|---|---|---|---|---|
| 1 | 38.7 | 38.7 | 38.7 | 38.7 | 38.8 | 38.8 | 38.8 | 38.8 | 38.8 | 38.1 | 38.8 | 38.8 |
| 2 | 26.6 | 26.6 | 26.7 | 26.7 | 26.7 | 26.7 | 26.8 | 26.7 | 26.7 | 26.3 | 26.8 | 26.7 |
| 3 | 88.9 | 89.0 | 88.5 | 88.5 | 89.1 | 89.1 | 88.7 | 88.7 | 88.7 | 87.7 | 88.7 | 88.7 |
| 4 | 39.6 | 39.6 | 39.7 | 39.7 | 39.7 | 39.7 | 39.8 | 39.8 | 39.8 | 39.6 | 39.8 | 39.7 |
| 5 | 56.1 | 56.1 | 56.2 | 56.2 | 56.2 | 56.2 | 56.3 | 56.2 | 56.2 | 55.3 | 56.2 | 56.2 |
| 6 | 18.3 | 18.3 | 18.3 | 18.3 | 18.3 | 18.3 | 18.3 | 18.3 | 18.8 | 18.3 | 18.3 | 18.3 |
| 7 | 36.1 | 36.1 | 36.1 | 36.0 | 36.1 | 36.1 | 36.0 | 36.1 | 36.0 | 36.6 | 36.0 | 36.1 |
| 8 | 37.6 | 37.5 | 37.5 | 37.5 | 37.5 | 37.5 | 37.5 | 37.5 | 37.5 | 36.8 | 37.2 | 37.2 |
| 9 | 53.0 | 53.0 | 53.0 | 53.0 | 53.0 | 53.0 | 53.0 | 53.1 | 53.0 | 52.4 | 53.0 | 52.9 |
| 10 | 37.2 | 37.25 | 37.3 | 37.3 | 37.2 | 37.1 | 37.1 | 37.1 | 37.2 | 36.7 | 37.4 | 18.3 |
| 11 | 21.8 | 21.8 | 21.8 | 21.7 | 21.7 | 21.7 | 21.7 | 21.7 | 21.7 | 21.1 | 21.7 | 21.7 |
| 12 | 28.5 | 28.6 | 28.5 | 28.6 | 28.5 | 28.6 | 28.5 | 28.6 | 28.6 | 27.7 | 28.4 | 28.4 |
| 13 | 36.8 | 37.1 | 37.1 | 37.1 | 37.2 | 37.1 | 37.2 | 37.23 | 37.1 | 35.8 | 36.0 | 36.1 |
| 14 | 53.7 | 53.5 | 53.7 | 53.5 | 53.7 | 53.5 | 53.7 | 53.5 | 53.5 | 53.0 | 53.8 | 53.8 |
| 15 | 36.9 | 36.9 | 36.8 | 36.9 | 36.8 | 36.9 | 36.9 | 36.9 | 36.9 | 35.8 | 37.5 | 37.5 |
| 16 | 110.6 | 110.3 | 110.5 | 110.3 | 110.5 | 110.3 | 110.5 | 110.3 | 110.3 | 109.1 | 110..3 | 110.2 |
| 17 | 54.0 | 51.3 | 54.0 | 51.3 | 54.0 | 51.3 | 54.0 | 51.3 | 51.3 | 50.1 | 55.1 | 55.1 |
| 18 | 18.9 | 18.8 | 18.9 | 18.8 | 18.8 | 18.8 | 18.8 | 18.8 | 18.8 | 18.4 | 18.8 | 18.8 |
| 19 | 16.3 | 16.3 | 16.3 | 16.3 | 16.3 | 16.3 | 16.3 | 16.3 | 16.3 | 15.9 | 16.3 | 16.6 |
| 20 | 71.6 | 68.6 | 68.5 | 71.9 | 68.5 | 71.8 | 68.5 | 71.8 | 71.8 | 70.6 | 75.2 | 75.5 |
| 21 | 30.0 | 27.2 | 30.0 | 27.2 | 29.9 | 27.1 | 30 | 27.1 | 27.2 | 26.3 | 25.1 | 25.1 |
| 22 | 45.5 | 46.3 | 45.5 | 46.2 | 45.5 | 46.3 | 45.5 | 46.2 | 46.2 | 44.5 | 41.6 | 41.6 |
| 23 | 68.5 | 66.1 | 68.5 | 66.1 | 68.5 | 66.1 | 68.5 | 66.1 | 66.1 | 65.7 | 68.7 | 68.8 |
| 24 | 127.1 | 124.2 | 127.1 | 124.1 | 127.1 | 124.1 | 127.1 | 124.1 | 124.1 | 123.2 | 127.4 | 127.4 |
| 25 | 134.1 | 132.9 | 134.0 | 132.8 | 134.0 | 132.9 | 134.2 | 132.9 | 132.9 | 132.2 | 133.8 | 133.8 |
| 26 | 25.5 | 26.0 | 25.5 | 26.0 | 25.5 | 26.0 | 25.5 | 26.0 | 26.0 | 25.9 | 25.7 | 25.7 |
| 27 | 18.4 | 18.5 | 18.3 | 18.4 | 18.3 | 18.4 | 18.3 | 18.4 | 18.4 | 18.4 | 18.3 | 18.3 |
| 28 | 28.0 | 28.0 | 28.0 | 28.0 | 27.8 | 27.8 | 27.8 | 27.8 | 27.8 | 27.4 | 27.8 | 27.8 |
| 29 | 16.8 | 16.8 | 16.7 | 16.7 | 16.5 | 16.5 | 16.5 | 16.5 | 16.5 | 16.3 | 16.6 | 16.3 |
| 30 | 65.8 | 65.9 | 65.8 | 65.9 | 65.8 | 65.9 | 65.7 | 65.8 | 65.8 | 64.9 | 65.9 | 66.0 |
| | 3-O-Glc | 3-O-Glc | 3-O-Ara(p) | 3-O-Ara(p) | 3-O-Glc | 3-O-Glc | 3-O-Ara(p) | 3-O-Ara(p) | 3-O-Ara(p) | 3-O-Ara(p) | 3-O-Ara(p) | 3-O-Glc |
| 1' | 105.9 | 105.9 | 107.2 | 107.2 | 105.1 | 105.1 | 105.6 | 105.6 | 105.5 | 105.5 | 105.5 | 105.0 |
| 2' | 75.5 | 75.4 | 71.8 | 71.9 | 79.1 | 79.1 | 77.0 | 76.9 | 76.6 | 70.1 | 77.0 | 79.2 |
| 3' | 88.9 | 88.9 | 84.1 | 84.2 | 88.6 | 88.7 | 83.4 | 83.4 | 83.9 | 83.0 | 83.5 | 89.1 |
| 4' | 69.98 | 70.6 | 69.2 | 69.3 | 70.3 | 70.3 | 68.5 | 68.5 | 67.6 | 67.4 | 68.5 | 70.3 |
| 5' | 78.6 | 77.9 | 66.8 | 66.9 | 78.0 | 78.0 | 65.7 | 65.8 | 65.5 | 64.7 | 65.8 | 78.5 |
| 6' | 62.7 | 62.7 | | | 62.7 | 62.7 | | | | | — | 62.8 |
| | Glc | Glc | Glc | Glc | Ara(f) | Ara(f) | Ara(f) | Ara(f) | Ara(f) | Glc | Ara(f) | Ara(f) |
| 1'' | 106.3 | 106.3 | 106.2 | 106.3 | 110.0 | 110.0 | 110.4 | 110.3 | 110.1 | 104.4 | 110.2 | 110.0 |
| 2'' | 74.4 | 74.0 | 75.7 | 75.7 | 83.7 | 83.7 | 83.7 | 83.8 | 83.6 | 74.9 | 83.9 | 83.8 |
| 3'' | 78.2 | 78.2 | 78.3 | 78.4 | 77.7 | 77.7 | 78.4 | 78.0 | 77.8 | 76.9 | 77.9 | 78.0 |
| 4'' | 68.5 | 68.6 | 71.6 | 71.6 | 85.0 | 85.0 | 85.1 | 85.0 | 84.9 | 70.1 | 83.8 | 85.0 |
| 5'' | 77.9 | 78.7 | 78.6 | 78.6 | 62.2 | 62.2 | 62.2 | 62.2 | 62.0 | 73.9 | 62.2 | 62.2 |
| 6'' | 62.5 | 62.5 | 62.7 | 62.7 | | | | | | 67.4 | — | — |
| | | | | | Glc | Glc | Glc | Glc | Glc | | Glc | Glc |
| 1''' | | | | | 104.7 | 104.7 | 104.9 | 104.9 | 104.9 | | 104.9 | 104.7 |
| 2''' | | | | | 75.5 | 75.4 | 75.2 | 75.2 | 74.9 | | 75.1 | 75.7 |
| 3''' | | | | | 78.4 | 78.5 | 76.9 | 78.0 | 77.4 | | 78.1 | 77.7 |
| 4''' | | | | | 71.6 | 71.6 | 71.6 | 71.5 | 70.9 | | 71.5 | 71.6 |
| 5''' | | | | | 78.4 | 78.5 | 78.1 | 78.4 | 76.1 | | 78.4 | 78.0 |
| 6''' | | | | | 62.4 | 62.4 | 62.6 | 62.6 | 67.6 | | 62.6 | 62.4 |

TABLE 2-continued

<sup>13</sup>C NMR data of *Bacopa* Saponins

| C | 1 | 2 | 3 | 4 | 5 | 6 | 7 | 8 | 9 | 10 | 11 | 12 |
|---|---|---|---|---|---|---|---|---|---|----|----|----|
|   |   |   |   |   |   |   |   |   |   |    | 20-O-Ara(p) | 20-O-Ara(p) |
|   |   |   |   |   |   |   |   |   |   |    | 98.6 | 98.8 |
|   |   |   |   |   |   |   |   |   |   |    | 72.9 | 73.1 |
|   |   |   |   |   |   |   |   |   |   |    | 75.1 | 75.0 |
|   |   |   |   |   |   |   |   |   |   |    | 69.2 | 69.3 |
|   |   |   |   |   |   |   |   |   |   |    | 66.2 | 66.6 |

All the $^1$H NMR spectra were measured in D$_5$-pyridine solvent. The $^{13}$C NMR spectra of all the saponin compounds, except 10, were measured in D$_5$-pyridine. The spectrum of 10 was recorded in D$_6$-DMSO. The $^1$H NMR spectra were measured on 400 MHz spectrometer instrument and $^{13}$C NMR spectra were measured on 100 MHz instrument.

EXAMPLE 2

Process for enriched *Bacopa* saponin fraction (Method I): An alcoholic or hydroalcoholic extract is prepared in the conventional manner from dried plant materials of *Bacopa monnieri*. After removing the solvents by evaporation preferably under vacuum to a dry powder, the dry powder contains 15% of total saponins, by HPLC. This mixture was dispersed in n-butanol and the insolubles were separated by filtration. The soluble portion was washed successively with water, 2% aqueous NaOH and water again. The n-butanol layer was evaporated preferably under vacuum to obtain a dry powder, whose total saponin content, as determined by HPLC analysis is 72%. Optionally, this dry powder was washed with acetone and dried to obtain a fraction enriched to 75% total saponins. This alkali washed material was dissolved in methanol and treated with charcoal. The mixture was filtered and the filtrate was evaporated to yield 85% total saponins as a dry powder. The dry powder was subjected to flash column chromatography over silica gel using mixtures of chloroform, methanol and water. The fractions were eluted with solvents of increasing polarity starting from chloroform/methanol (9:1) to chloroform/methanol/water (8:2:0.5). The fractions containing diglycosidic, triglycosidic, sulfated and tetraglycosidic saponins were combined and evaporated under vacuum to obtain a fraction enriched to 97% of total saponines. The absolute percentages of individual components in the enriched fraction were measured using HPLC method of analysis by comparison pure authentic compounds. The total *Bacopa* saponin concentration is obtained by addition of individual concentrations. The following is the summary of HPLC analysis of the enriched fraction obtained by the present invention.

HPLC analysis (total saponin fraction from silica column): 3-O-[β-D-glucopyranosyl-(1→3)-β-D-glucopyranosyl] jujubogenin (bacopaside N1, of general formula 1): 0.23%; 3-O-[β-D-glucopyranosyl-(1→3)-β-D-glucopyranosyl] pseudojujubogenin (bacopaside N2, of general formula 2): 0.55%; 3-O-[β-D-glucopyranosyl-(1→3)-α-L-arabinopyranosyl] jujubogenin (bacopaside IV, of general formula 3): 1.76%; 3-O-[β-D-glucopyranosyl-(1→3)-α-L-arabinopyranosyl] pseudojujubogenin (bacopaside V, of general formula 4): 0.75%; 3-O-[β-D-glucopyranosyl-(1→3)-O-{α-L-arabinofuranosyl-(1→2)}-O-(β-D-glucopyranosyl)oxy] jujubogenin (bacoside A3, of general formula 5): 22.49%; 3-O-[α-L-arabinofuranosyl-1→2)-{β-D-glucopyranosyl-(1→3)}-β-D-glucopyranosyl] pseudojujubogenin (bacopaside II, of general formula 6): 12.6%; 3-O-[α-L-arabinofuranosyl-(1→2)-{β-D-glucopyranosyl-(1→3)-}-α-L-arabinopyranosyl] jujubogenin (bacopaside X, of general formula 7): 24.55%; 3-O-[β-D-glucopyranosyl-(1→3)-{α-L-arabinofuranosyl-(1→2)}-α-L-arabinopyranosyl] pseudojujubogenin (bacopasaponin C, of general formula 8): 15.01%; 3-O-[α-L-arabinofuranosyl-(1→2)-{6-O-sulphonyl-β-D-glucopyranosyl-(1→3)}-α-L-arabinopyranosyl] pseudojujubogenin (bacopaside I, of general formula 9): 8.24%; 3-O-[{6-O-sulfonyl-β-D-glucopyranosyl-(1 3)}-α-L-arabinopyranosyl] pseudojujubogenin (bacopaside III, of general formula 10): 0.9%; 3-O-[β-D-glucopyranosyl-(1→3)-{α-L-arabinofuranosyl-(1→2)}-α-L-arabinopyranosyl]-20-O-(α-L-arabinopyranosyl) jujubogenin (bacopasaponin E, of general formula 11): 3.85%; 3-O-[β-D-glucopyranosyl-(1→3)-{α-L-arabinofuranosyl-(1→2)}-β-D-glucopyranosyl]-20-O-(α-L-arabinopyranosyl) jujubogenin (bacopasaponin F, of general formula 12): 5.93%. A fraction enriched up to 100% of total glycosides of jujubogenin and psudojujubogenin was obtained by crystallization using methanol/ethyl acetate. Note: No trivial name has been assigned in the literature to the known saponin, 3-O-[α-L-arabinofuranosyl-(1→2)-{β-D-glucopyranosyl-(1→3)-}-α-L-arabinopyranosyl] jujubogenin (of general formula 7). For convenience a short name, bacopaside X, has been assigned by the inventors.

EXAMPLE 3

Process for enriched *Bacopa* saponin fraction (Method II): An alcoholic or hydroalcoholic extract is prepared in the conventional manner from dried plant materials of *Bacopa monniera*. After removing the solvents by evaporation preferably under vacuum a dry powder, the powdered extract contains approximately 15% of mixtures of *Bacopa* saponins by HPLC. This mixture was dispersed in n-butanol and the insolubles were separated by filtration. The soluble portion was washed successively with water, 2% NaOH and water again. The n-butanol layer was evaporated, preferably under vacuum to obtain a dry powder, which is a 60-65% mixture of total saponins. The dry powder was subjected to column chromatography over silica gel using mixtures of chloroform/methanol (8.2:1.8) to chloroform/methanol/water (8:2:0.5). The fractions containing various saponin compounds were combined and evaporated under reduced pressure to obtain a mixture containing 80-90% of total saponins. The dry powder was dissolved in methanol and treated with charcoal and filtered. The methanol solution was evaporated under reduced pressure to obtain a mixture containing up to 100% total saponins.

EXAMPLE 4

Process for separation of fractions containing diglycosidic saponins triglycosidic saponins, tetraglycosidic saponins and sulfated saponins: The mixture of *Bacopa* saponins, obtained after charcoal treatment as described in example 2, is subjected to silica column chromatography using solvents with a slow gradient of increasing polarity starting from chloroform. The fractions eluted with chloroform/methanol 9:1 were monitored and the identical fractions combined to yield a mixture that was enriched up to 81% of total diglycosidic saponins, 3-O-[β-D-glucopyranosyl-(1→3)-β-D-glucopyranosyl] jujubogenin (bacopaside N1, of general formula 1), 3-O-[β-D-glucopyranosyl-(1→3)-β-D-glucopyranosyl] pseudojujubogenin (bacopaside N2, of general formula 2), bacopaside IV (of general formula 3) and bacopaside V, of general formula 4). The fractions that were eluted with chloroform/methanol (8.5:1.5) were similarly monitored and combined and evaporated to yield a mixture of triglycosidic saponins, bacoside $A_3$, (of general formula 5), bacopaside II (of general formula 6), 3-O-[α-L-arabinofuranosyl-(1→2)-{β-D-glucopyranosyl-(1→3)-}-α-L-arabinopyranosyl] jujubogenin (bacopaside X, of general formula 7) and bacopasaponin C (of general formula 8) at a total overall concentration of up to 99% by HPLC analysis. The fractions that were obtained on elution with chloroform/methanol/water 8.2:1.8:0.03 were combined and evaporated to obtain sulfated saponins to yield a mixture of bacopaside I (of general formula 9) and bacopaside III (of general formula 10). Finally the fractions that were obtained on elution with chloroform/methanol/water 8:2:0.5 were combined and evaporated to obtain tetraglycosidic saponins, bacopasaponin E (of general formula 11) and bacopasaponin F (of general formula 12). The foregoing diglycosidic, triglycosidic tetraglycosidic mixtures were further enriched up to 100% by rechromatography over silica flash column or by crystallization. The absolute percentages of individual components were measured using HPLC method of analysis.

Diglycosidic fraction: 3-O-[β-D-glucopyranosyl-(1→3)-β-D-glucopyranosyl] jujubogenin (bacopaside N1, of general formula 1): 2.24%; 3-O-[β-D-glucopyranosyl-(1→3)-β-D-glucopyranosyl] pseudojujubogenin (bacopaside N2, of general formula 2): 8.98%; bacopaside IV (of general formula 3): 41.5%; bacopaside V (of general formula 4): 28.2%.

Triglycosidic fraction: Bacoside $A_3$ (of general formula 5): 29.45%; Bacopaside II (of general formula 6): 15.81%; 3-O-[α-L-arabinofuranosyl-(1→2)-{β-D-glucopyranosyl-(1→3)-}-β-L-arabinopyranosyl] jujubogenin (bacopaside X, of general formula 7): 33.23%; Bacopasaponin C, of general formula 8): 21.38%.

EXAMPLE 5

Process for producing a fraction containing a mixture of diglycosidic and triglycosidic saponins: The mixture of Bacopa saponins, obtained after charcoal treatment as described in example 2, is subjected to silica column chromatography using solvents of increasing polarity starting from chloroform. The fractions eluted with chloroform/methanol (8.2:1.8) were monitored, and the fractions containing the saponins were combined and evaporated to obtain a fraction that was enriched to 90% of total saponins (of general formula 1 to 8). The residue was dissolved in methanol, treated with carbon, separated the carbon by filtration and the solvent was evaporated from the mother liquor to obtain a fraction enriched to 97% of total diglycosidic and triglycosidic saponins (of general formula 1 to 8).

HPLC analysis (the concentrations of individual components are expressed in absolute %): 3-O-[β-D-glucopyranosyl-(1→3)-β-D-glucopyranosyl] jujubogenin (bacopaside N1, of general formula 1): 0.62%; 3-O-[β-D-glucopyranosyl-(1→3)-β-D-glucopyranosyl] pseudojujubogenin (bacopaside N2, of general formula 2): 0.95%; bacopaside IV (of general formula 3): 2.22%; bacopaside V (of general formula 4): 0.93%; bacoside $A_3$ (of general formula 5): 30.09%; bacopaside II, (of general formula 6): 13.34%; 3-O-[α-L-arabinofuranosyl-(1→2)-{β-D-glucopyranosyl-(1→3)-}-α-L-arabinopyranosyl] jujubogenin (bacopaside X, of general formula 7): 30.69%; bacopasaponin C (of general formula 8): 17.88%.

EXAMPLE 6

Method for the estimation of *Bacopa* saponins from enriched saponin fraction and bacosides A & B: HPLC (high pressure liquid chromatography) experiments were performed on Shimadzu system equipped with LC10 ATVP pumps and SPD M10 AVP PDA detector and auto injector. For all the separations a Phenomenex Luna C 18 column (4.6×250 mm, 5 micron particle size) was used. All the experiments were done in isocratic elution using a mixture of 0.05 M sodium sulphate (pH 2.3) and acetonitrile (68.5:31.5) as mobile phase. The flow rate was adjusted to 1 ml/min and the column temperature was maintained at 30° C. The detector wavelength was adjusted to 205 nm. The run time for each separation was 75 min. The size of sample injection was 20 μl, and the solvent for injection was 1:1, 0.05 M sodium sulphate (pH 2.3)/acetonitrile. The in-house reference standards were used for estimation. Peaks in the chromatogram for total *Bacopa* saponin fraction, were initially assigned by spiking the experimental sample with individual standard compounds. Standard solution was prepared by weighing accurately about 5.0 mg of each sample of in-house reference standard in to a 10 ml volumetric flask and dissolve and make up the volume with the injection solvent. Similarly, sample preparation was done by weighing accurately about 15.0 mg of experimental sample in to a 10 ml volumetric flask, dissolve and make up the volume with solvent. Both standard and sample solutions were filtered through Waters Millipore, 0.45μ membrane filter before injecting. Absolute concentration of individual saponin was calculated by the formula, percentage of individual component=peak area of the component in the sample×concentration of the standard×purity of standard/peak area of standard×concentration of sample. The total absolute concentration of *Bacopa* saponin fraction was obtained by the addition of individual concentrations of all the components in the enriched fraction together.

EXAMPLE 7

Brine shrimp lethality assay: Brine shrimp lethality (BSL) assay is a simple bench top bioassay developed by McLaughlin, et. al. (*Studies in Natural Product Chemistry,* 9, page 383, 1991 and *Am. Chem. Soc. Symp. Series,* 534, page 114, 1992) and the results obtained by this assay have been reported to be corroborative with the cytotoxicities determined in 9KB and 9PS cells. The procedure involves hatching Artemia salina cysts in a cone shaped vessel and collecting active nauplii after 48 hr and treating with known concentrations of test substances and vehicle (control) in tubes each tube containing 10 nauplii and checking viability/mortality after 24 hr. Percentage lethality was calculated by comparing mean values of control and test sets of three tubes each. $LC_{50}$ values were obtained from the graph plotted micro molar concentration against percent lethality. The inhibitory concentrations for *Bacopa* extracts and enriched fractions were summarized in table 3.

TABLE 3

BRINE SHRIMP LETHALITY DATA OF ENRICHED *BACOPA* SAPONIN FRACTIONS

| S. No | Name of test substance | Total *Bacopa* saponin concentraction | $IC_{50}$ µg/mL |
|---|---|---|---|
| 1 | *Bacopa* crude extract | 14.8% | 80 |
| 2 | *Bacopa* 50% commercial sample | 22.6% | 39 |
| 3 | *Bacopa* charcoal treated fraction | 80% | 25 |
| 4 | *Bacopa* enriched column fraction | 97% | 12.5 |

IC: Inhibitory concentration

Though the foregoing examples describe a specific embodiment of the present invention, obvious equivalents and modifications known to persons skilled in the art are not excluded from the scope of the appended claims.

The invention claimed is:

1. A process for producing an enriched fraction containing up to 100% of total saponins from an extract of *Bacopa* species, comprising:
   subjecting plant materials of *Bacopa* species to extraction using a solvent selected from the group consisting of water, aqueous organic solvent, an organic solvent, and mixtures thereof;
   concentrating the extract under vacuum effective for forming a dry powder;
   dispersing the dry powder in a polar organic solvent effective for forming a polar solvent extract;
   washing the polar solvent extract after removal of insolubles therefrom, with water, 2% aqueous sodium hydroxide and water;
   concentrating the extract thereafter under vacuum effective for forming a dry mass containing 60-75% of total saponins;
   dissolving the dry mass in alcohol or aqueous alcohol effective for forming an alcohol or aqueous alcohol solution and then treating the solution with an adsorbent, the adsorbent including charcoal;
   concentrating the solution under reduced pressure after removing the adsorbent therefrom to form a dry mass containing 75-85% total *Bacopa* saponins;
   chromatographically separating the dry mass to a fraction containing more than 95% of total saponins using silica gel; and
   crystallizing the fraction in a suitable solvent to obtain a fraction containing at least about 95% of *Bacopa* saponins as estimated by high pressure liquid chromatography, wherein the concentration of *Bacopa* saponins in the fraction is greater than in a product prepared without washing with aqueous alkali and without treating with an adsorbent.

2. The process as claimed in claim 1, wherein plant material is selected from the group consisting of *Bacopa carolliniana, Bacopa egenii, Bacopa innominata, Bacopa monnieri, Bacopa procumbens, Bacopa repens, Bacopa rotundifolia, Bacopa stricta, Zizyphus joazeiro* and *Colubrina retusa*, and mixtures thereof, and the solvent of extraction is selected from the group consisting of ethyl alcohol, methyl alcohol, hydroalcohol, water, and mixtures thereof.

3. The process as claimed in claim 1, wherein the polar organic solvent is selected from the group consisting of ethyl acetate, n-butyl acetate, ethyl propionate, n-butanol, and combinations thereof, effective for obtaining a fraction enriched to 20-35% of total *Bacopa* saponins.

4. The process as claimed in claim 1, wherein the polar organic solvent extract is washed with water, followed by alkali solution to obtain a fraction containing 60 to 75% *Bacopa* saponins.

5. The process as claimed in claim 1, wherein the alkali washed organic extract is washed with water, and the organic layer evaporated and dried under vacuum to obtain a fraction enriched to 60-75% total *Bacopa* saponins as dry powder.

6. The process as claimed in claim 1, comprising dissolving the concentrated and powdered, water or organic solvent or aqueous organic solvent extract of the *Bacopa* species in 2% aqueous alkali solution first and then twice washing with the polar organic solvent, separating an aqueous layer and washing an organic layer with water to free it from contaminants.

7. The process as claimed in claim 1, wherein said alcohol for dissolution of alkali washed powdered extract is selected from the group consisting of methanol, ethanol, propanol, isopropanol, n-butanol, isobutanol, t-butanol and their aqueous solutions.

8. The process as claimed in claim 1, comprising washing the dry powdered extract obtained after charcoal treatment and evaporation, with an organic solvent, to obtain a fraction enriched to 85-90% of total saponins.

9. The process as claimed in claim 1, wherein eluants for normal phase chromatography are solvents selected from the group consisting of dichloroethane, dichloromethane, chloroform, ethyl acetate, methanol, ethanol, propanol, isopropanol, butanol, isobutanol, t-butanol, water and mixtures thereof.

10. The process as claimed in claim 1, wherein support for reversed phase chromatography of alkali washed and charcoal treated *Bacopa* saponin fraction is C8 or C18 bonded reverse phase silica and eluants are mixtures of water with one or more solvents selected from the group consisting of acetone, acetonitrile, dioxane, ethanol, methanol, n-propanol, isopropanol, n-butanol and tert-butanol.

11. The process as claimed in claim 1, wherein said chromatography fraction enriched to more than 95% of total saponins is further enriched up to 100% of total saponins, by crystallization from a suitable solvent.

12. The process as claimed in claim 11, wherein the solvent of crystallizaton is selected from the group consisting of ethyl acetate, acetone, acetonitrile, dioxane, ethanol, methanol, n-propanol, isopropanol, n-butanol, t-butanol, and combinations thereof.

13. The method of estimating total and individual *Bacopa* saponins contained in the enriched *Bacopa* saponins fraction obtained by the process as claimed in claim 1, comprising separating the fraction with HPLC (high pressure liquid chromatography), wherein a HPLC column has C 18 silica, and the separation is effected at a flow rate of 0.2 ml to 0.6 ml/min, at a column temperature of 20 to 40° C., a gradient or isocratic mobile phase being mixtures of aqueous sodium sulfate, aqueous acetic acid and acetonitrile, strength being 0.05M sodium sulphate, 0.1% acetic acid, acetonitrile in a proportion of 40:40:20 and separating the saponins from the different mobile phases.

14. A method of treating cognitive, anxiety, depression or epileptic disorders in a subject in need of treatment, the method comprises: administering the enriched *Bacopa* saponin composition prepared by the process as claimed in claim 1, in dietary and nutraceutical supplements or formulations to the subject in need.

15. A method of treating Alzheimer's disease, hypothyroidism, asthma or bronchitis in a subject in need of treatment, wherein the method comprises administering the enriched *Bacopa* saponin composition prepared by the process as claimed in claim 1, or formulation containing the composition to the subject in need.

16. A method for enhancement of at least one cognitive function related to memory, learning ability and concentration for a person in need thereof, wherein the method comprises administering to the person in need the enriched *Bacopa* saponin composition prepared by the process as claimed in claim 1, or formulations containing the composition.

17. A method for improving the health condition and maintaining the health of an animal in need thereof, the method comprising administering to the animal in need the enriched *Bacopa* saponin composition prepared by the process as claimed in claim 1, or pharmaceutically acceptable salts thereof, or formulations containing the composition or the salts, or with a pharmaceutically acceptable carrier or diluents.

18. An enriched saponin fraction according to claim 1, wherein the said fraction contains at least one diglycosidic saponin selected from the group consisting of 3-O-[β-D-glucopyranosyl-(1→3)-β-D-glucopyranosyl] jujubogenin and 3-O-[β-D-glucopyranosyl-(1→3)-β-D-glucopyranosyl] pseudojujubogenin.

19. The process as claimed in claim 4, wherein said alkali solution is 2% NaOH or 2% KOH in water.

20. The method of claim 13, wherein the HPLC column has C 18 silica of 5 µ, 4.6 mm×150 mm dimensions, and UV detection at 260-270 nm wave length.

21. The process of claim 1, wherein the enriched fraction comprises: 1) 3-O-[β-D-glucopyranosyl-(1→3)-β-D-glucopyranosyl] jujubogenin; 2) and 3-O-[β-D-glucopyranosyl-(1→3)-β-D-glucopyranosyl] pseudojujubogenin; 3) Bacopaside IV; 4) Bacopaside V; 5) Bacopaside A3; 6) Bacopaside II; 7) Bacopaside X; 8) Bacopasaponin C; 9) Bacopaside I; 10) Bacopaside III; 11) Bacopasaponin E; and 12) Bacopasaponin F.

22. A process for producing an enriched fraction containing up to 100% of total saponins from an extract of *Bacopa* species, comprising:
    subjecting plant materials of *Bacopa* species to extraction using a solvent selected from the group consisting of water, aqueous organic solvent, an organic solvent, and mixtures thereof;
    concentrating the extract under vacuum effective for forming a dry powder;
    dispersing the dry powder in a polar organic solvent effective for forming a polar solvent extract;
    washing the polar solvent extract after removal of insolubles therefrom, with an effective amount of aqueous sodium hydroxide and water to provide at least about 95% of *Bacopa* saponins after treatment with an adsorbent and crystallization;
    concentrating the extract thereafter under vacuum effective for forming a dry mass containing 60-75% of total saponins;
    dissolving the dry mass in alcohol or aqueous alcohol effective for forming an alcohol or aqueous alcohol solution and then treating the solution with the adsorbent, the adsorbent including charcoal;
    concentrating the solution under reduced pressure after removing the adsorbent therefrom to form a dry mass containing 75-85% total *Bacopa* saponins;
    chromatographically separating the dry mass to a fraction containing more than 95% of total saponins using silica gel; and
    crystallizing the fraction in a suitable solvent to obtain a fraction containing the at least about 95% of *Bacopa* saponins, as estimated by high pressure liquid chromatography, wherein the concentration of *Bacopa* saponins in the fraction is greater than in a product prepared without washing with aqueous alkali and without treating with an adsorbent.

23. The process of claim 22 wherein the step of washing the polar solvent extract with aqueous alkali provides at least about 20% further enrichment of total saponins over a step of washing with water alone.

24. The process of claim 22 wherein treating the solution with the adsorbent provides a further enrichment of total saponins by at least about 5%.

\* \* \* \* \*